(12) United States Patent
Nilsen-Hamilton (10) Patent No.: US 7,115,369 B2
(45) Date of Patent: Oct. 3, 2006

(54) FUNCTIONAL NUCLEIC ACID PROBES AND USES THEREOF

(75) Inventor: Marit Nilsen-Hamilton, Ames, IA (US)

(73) Assignee: Iowa State University Research Foundation, Inc., Ames, IA (US)

( * ) Notice: Subject to any disclaimer, the term of this patent is extended or adjusted under 35 U.S.C. 154(b) by 531 days.

(21) Appl. No.: 10/096,872

(22) Filed: Mar. 14, 2002

(65) Prior Publication Data

US 2002/0150996 A1 Oct. 17, 2002

Related U.S. Application Data

(60) Provisional application No. 60/275,695, filed on Mar. 15, 2001.

(51) Int. Cl.
*C12Q 1/68* (2006.01)
(52) U.S. Cl. .......................... 435/6; 536/24.1
(58) Field of Classification Search .............. 702/27, 702/20, 19; 435/6, 29, 91, 23; 514/44; 536/23.1, 536/24.1
See application file for complete search history.

(56) References Cited

U.S. PATENT DOCUMENTS

| | | |
|---|---|---|
| 5,270,163 A | 12/1993 | Gold et al. |
| 5,475,096 A | 12/1995 | Gold et al. |
| 6,180,348 B1 | 1/2001 | Li |
| 6,261,774 B1 | 7/2001 | Pagratis et al. |
| 6,680,377 B1 * | 1/2004 | Stanton et al. ............ 536/22.1 |

2004/0171039 A1 * 9/2004 Bruchez et al. ................ 435/6

OTHER PUBLICATIONS

Porta, H. et al.—"An Allosteric Hammerhead Ribozyme," Bio/Technology, vol. 13, Feb. 1995, pp. 161-164.
Hermann, T. et al.—"Adaptive Recognition by Nucleic Acid Aptamers," Science, vol. 287, Feb. 4, 2000, pp. 820-825.
Soukup, G. et al.—"Nucleic acid molecular switches," Nanotechnology, vol. 17, Dec. 1999, pp. 469-476.
Stojanovic, M. et al.—"Catalytic Molecular Beacons," CHEMBIOCHEM 2001, vol. 2, pp. 411-415.
Jenne, A. et al.—"Rapid identification and characterization of hammerhead-ribozyme inhibitors using fluorescence-based technology," Nature Biotechnology, vol. 19, Jan. 2001, pp. 56-61.
Sanjay Tyagi, et al.—"Multicolor molecular beacons for allele discrimination," Nature Biotechnology, vol. 16, Jan. 1998, pp. 49-53.
Sanjay Tyagi, et al.—"Molecular Beacons: Probes that Fluoresce upon Hybridization," Nature Biotechnology, vol. 14, Mar. 1996, pp. 303-308.

(Continued)

*Primary Examiner*—Michael Borin
*Assistant Examiner*—Jerry Lin
(74) *Attorney, Agent, or Firm*—Dickstein Shapiro LLP (57) ABSTRACT

The present invention provides functional nucleic acid probes, and methods of using functional nucleic acid probes, for binding a target to carry out a desired function. The probes have at least one functional nucleic acid, at least one regulating nucleic acid, and at least one attenuator. The functional nucleic acid is maintained in an inactive state by the attenuator and activated by the regulating nucleic acid only in the presence of a regulating nucleic acid target. In its activated state the functional nucleic acid can bind to its target to carry out a desired function, such as generating a signal, cleaving a nucleic acid, or catalyzing a reaction.

17 Claims, 5 Drawing Sheets

OTHER PUBLICATIONS

Doug Irvine, et al.—"SELEXION Systematic Evolution of Ligands by Exponential Enrichment with Integrated Optimization by Nonlinear Analysis," J. Mol. Biol., 1991, 222, pp. 739-761.

Edward N. Brody, et al.—"Aptamers as therapeutic and diagnostic agents," J. Biotechnology, Mar. 2000, 74(1), pp. 5-13.

Dinshaw J. Patel, et al.—"Structure, recognition and discrimination in RNA aptamer complexes with cofactors, amino acids, drugs and aminoglycoside antibiotics," Molecular Biotechnology, Mar. 2000, 74(1), pp. 39-60.

Thomas Hermann, et al.—"Adaptive Recognition by Nucleic Acid Aptamers," Science, vol. 287, Feb. 4, 2000, pp. 820-825.

Y. Hirose, et al.—"High Speed Memory Behavior and Reliability of an Amorphous $As_2S_3$ Film Doped with Ag," Short Notes, phys. stat. sol. (a)61, 1980, pp. K187-190.

Sengen Sun—"Technology evaluation: SELEX, Gilead Sciences Inc.," Selex Sun, Current Opinion in Molecular Therapeutics, vol. 2, No. 1, 2000, pp. 100-105.

* cited by examiner

SEQUENCE LISTING

<160> NUMBER OF SEQ ID NOS: 5

<210> SEQ ID NO 1
<211> LENGTH: 26
<212> TYPE: DNA
<213> ORGANISM: Artificial Sequence
<220> FEATURE:
<223> OTHER INFORMATION: Description of Artificial Sequence: Synthetic
      DNA-ATP aptamer

<400> SEQUENCE: 1

```
cctggggag tattgcggag gaaggg                                          26

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      antisense nucleic acid

<400> SEQUENCE: 2
tactcctcag ggccggcgg                                                 19

<210> SEQ ID NO 3
<211> LENGTH: 8
<212> TYPE: DNA
<213> ORGANISM: Artificial Sequence
<220> FEATURE:
<223> OTHER INFORMATION: Description of Artificial Sequence: Synthetic
      attenuator

<400> SEQUENCE: 3 ccgcaata                                                              8

<210> SEQ ID NO 4
<211> LENGTH: 19
<212> TYPE: DNA
<213> ORGANISM: Artificial Sequence
<220> FEATURE:
<223> OTHER INFORMATION: Description of Artificial Sequence: Synthetic
      segment of the RAS oncogene mRNA

<400> SEQUENCE: 4
atgaggagtc ccggccgcc                                                 19

<210> SEQ ID NO 5
<211> LENGTH: 53
<212> TYPE: DNA
<213> ORGANISM: Artificial Sequence
<220> FEATURE:
<223> OTHER INFORMATION: Description of Artificial Sequence: Probe

<400> SEQUENCE: 5
cctgggggag tattgcggag gaagggtact cctcagggcc ggcggccgca ata           53
```

FUNCTIONAL NUCLEIC ACID PROBES AND USES THEREOF

CROSS-REFERENCE TO RELATED APPLICATIONS

This application claims priority to U.S. Provisional Patent Application No. 60/275,695 filed on Mar. 15, 2001 which is hereby incorporated by reference in its entirety.

STATEMENT REGARDING FEDERALLY SPONSORED RESEARCH OR DEVELOPMENT

The United States Government may have certain rights in this invention pursuant to Grant Number W-7405-Eng-82 from the Department of Energy, and National Institute of Health Grant No. R43CA102816.

REFERENCES

Several patents and other publications are referenced herein. Full citations for these publications are provided below. The disclosures of these publications are hereby incorporated herein by reference in their entirety, unless otherwise noted.

BACKGROUND OF THE INVENTION

Detection of nucleic acids is the cornerstone of biotechnology and molecular biology. Single-base pair mutations in a gene can be detected with great specificity and accuracy. The level of expression of a particular gene can be measured by detecting mRNA expression levels for the gene in a cell. Knowledge about the location, sequence, regulation, and expression of a gene yields information critical to the diagnosis and treatment of a variety of diseases.

Nucleic acid probes are typically short nucleic acid sequences used to detect, amplify, and quantify DNA and RNA for diagnostic and therapeutic applications. They are designed to specifically hybridize with particular complementary target nucleic acid sequences. Nucleic acid probes are labeled with radioactive or fluorescent tags in order to detect the presence or absence of the target nucleic acid sequence using a variety of techniques (e.g., fluorescent in-situ hybridization, Southern blot, Northern blot, and chromatography). While these techniques are useful for detecting the presence or absence of particular target sequences, their sensitivity depends on the amount of target nucleic acid present in the sample. Furthermore, living cells cannot be analyzed using these techniques since samples must be extracted, and fixed or frozen prior to analysis.

In order to increase the sensitivity of nucleic acid detection techniques, labeled probes are combined with amplification processes, such as PCR, to amplify and detect nucleic acids. The combination of probes and amplification processes has been especially useful in forensic applications where the nucleic acid of interest may only be present in extremely small quantities. Many disease conditions are diagnosed by comparing the amount of mRNA produced in a normal cell to a diseased cell. For example, increased expression of an oncogene may indicate the presence of a tumor cell. Amplification techniques, such as PCR, are non-linear and exponentially increase the amount of nucleic acid present in a sample. Thus, the amount of nucleic acid present in a sample subject to PCR is not representative of the amount of nucleic originally present in the sample. Nucleic acid amplification techniques are of limited use for quantifying the amount of nucleic acid present in a sample.

Previously, nucleic acids were thought to be a medium solely for storing, transporting, processing, and expressing genetic information. Recently, however, nucleic acids capable of additional functions have been identified. These "functional nucleic acids" can, for example, catalyze reactions or bind specifically to particular targets. The three-dimensional structure of functional nucleic acids provides the specificity necessary to bind other compounds much like the three-dimensional structure of an enzyme determines its specificity for a substrate. The small size, specificity, and ease of manipulation of nucleic acids can now be applied to functions traditionally associated with proteins (e.g., catalysis, receptors, and antibodies).

Molecular beacons are functional single-stranded DNA probes that can report the presence of specific nucleic acids. Molecular beacons are stem-loop shaped molecules containing a nucleotide sequence in the loop portion of the molecule complementary to a target DNA or RNA. Molecular beacons are labeled on one end with a fluorescent molecule and on the other with a quenching molecule. In its native hairpin structure, the quenching molecule is in close proximity with the fluorescent molecule and absorbs the light emission of the fluorescent molecule. When the complementary nucleotide sequence on the molecular beacon loop binds its target molecule, the molecular beacon undergoes a conformational change that opens up the stem-loop structure and causes the fluorescent molecule and the quenching molecule to move away from each other. The light emission from the fluorescent molecule is no longer quenched and the signal can be detected.

Molecular beacons are of limited use in generating amplified signals. The fluorescent signal of a molecular beacon is an integral part of the molecular beacon. Thus, the fluorescent molecule of the molecular beacon can generate only one signal in the presence of its target. The signal cannot be further amplified or altered by use of, for example, secondary labeled antibodies. The weak, unamplified signal generated by the molecular beacon is not able to penetrate living tissue sufficiently for use in non-invasive imaging.

Aptamers are functional synthetic nucleic acids optimized for high-affinity binding to targets (e.g., nucleic acids, proteins, and chemical compounds). Unlike naturally occurring nucleic acids, which are optimized with respect to transfer of genetic information, aptamers are selected on the basis of their ability to specifically bind their ligand. Systematic Evolution of Ligands by Exponential Enrichment (SELEX) is a process of selecting aptamers directed to a chosen ligand. See Hermann and Patel, *Science* 287, pp 820–825 (2000); U.S. Pat. Nos. 5,475,096, 5,595,877, 5,660,985, and 6,180,348. The SELEX process selects aptamers by screening random sequence libraries, retaining sequences that bind the chosen target molecule, and repeating the cycle with increasing levels of binding stringency. The selected aptamer is capable of binding a chosen target but not other molecules.

Ribozymes are functional nucleic acid molecules with enzymatic capabilities, including the ability to cleave nucleic acid molecules in a sequence-specific manner. The three-dimensional structure of a ribozyme, like a protein enzyme, determines the specificity of its interaction with a particular target. Allosteric ribozymes are ribozyme nucleic acid constructs having a ribozyme portion and an antisense nucleic acid portion. The activation of the ribozyme is regulated by the binding of the antisense nucleic acid to a complementary nucleic acid target. In the absence of the antisense target, the ribozyme is inactive. In the presence of the antisense target, the ribozyme is activated and capable of catalyzing a reaction.

Allosteric ribozymes may also include an attenuator sequence that binds completely or partially to the antisense nucleic acid portion as well as to the ribozyme portion. The "overlapping" attenuator sequence and the antisense target sequence compete for the binding site on the antisense sequence. In the presence of a sufficient amount of the antisense target sequence, the attenuator nucleic acid strand is displaced from the antisense sequence and the ribozyme is able to fold into its active conformation. However, strand displacement of the attenuator by the antisense target sequence has significant disadvantages. For example, the attenuator sequence must be designed to bind both the ribozyme and the antisense target sequence. This requirement limits the availability of compatible ribozyme-antisense sequence combinations. In addition, the antisense target sequence must compete for an overlapping binding site on the antisense sequence. Therefore, a relatively large quantity of the antisense target sequence is required in order to successfully displace the attenuator from the antisense sequence, thus resulting in reduced sensitivity of the probe.

It should be appreciated that there is a need for highly sensitive, functional nucleic acid probes capable of being activated to bind a target only in the presence of a particular ligand without being subject to foregoing limitations.

BRIEF SUMMARY OF THE INVENTION

The present invention provides nucleic acid probes for activating functional nucleic acids in the presence of a particular target. It has been unexpectedly discovered that nucleic acid probes having at least one functional nucleic acid (e.g., an aptamer or ribozyme), at least one regulating nucleic acid (e.g., antisense nucleic acid or aptamer), and at least one attenuator, are activated only in the presence of a regulating nucleic acid target. The modular nature of the nucleic acid probes provides great flexibility in designing custom probes using a variety of functional nucleic acids, regulating nucleic acids, and attenuators.

In one embodiment the functional nucleic acid probe is maintained in an inactive state by binding at least a portion of the functional nucleic acid to an attenuator. When the probe's regulating nucleic acid binds to its target, the conformation of the functional nucleic acid is modified resulting in removal of the attenuator and activation of the functional nucleic acid. The activated functional nucleic acid can then bind to its target. In other embodiments of the invention, the functional nucleic acid probes detects and quantifies nucleic acids in solution, in cells (e.g., fixed, frozen, and living cells), and in vivo for non-invasive imaging. The invention further provides functional nucleic acid probes that bind to a variety of signaling molecules (e.g., labeled proteins, labeled nucleic acids, and fluorescent compounds) and functional nucleic acid probes that catalyze reactions (e.g., site-specific cleavage of DNA or RNA).

DETAILED DESCRIPTION OF THE INVENTION

Reference will now be made in detail to the presently preferred embodiments of the invention, which serve to explain the principles of the invention. It is to be understood that the application of the teachings of the present invention to a specific problem or environment will be within the capabilities of one having ordinary skill in the art in light of the teachings contained herein.

The present invention provides functional nucleic acid probes, which, in one embodiment, include at least one functional nucleic acid, at least one regulating nucleic acid, and at least one attenuator. The functional nucleic acid is capable of binding to a specific target in order to carry out a desired function (e.g., catalyze a reaction, generate a signal, or cleave a nucleic acid). The regulating nucleic acid and the attenuator regulate the activity of the functional nucleic acid in response to environmental conditions (e.g., expression of an mRNA, the presence of an oncogenic protein, or the presence of a toxin). Preferably, the regulating nucleic acid is capable of activating the functional nucleic acid only when the regulating nucleic acid is bound to a regulating nucleic acid target. The attenuator preferably binds only to the functional nucleic acid, and maintains the functional nucleic acid in an inactive state so long as the regulating nucleic acid is not bound to the regulating nucleic acid target. The invention further provides methods of activating a functional nucleic acid to bind to a target by providing a functional nucleic acid, a regulating nucleic acid, and an attenuator wherein binding of the regulating nucleic acid to the regulating nucleic acid target induces the removal of the attenuator from the functional nucleic acid and activates the functional nucleic acid to bind its ligand.

In one embodiment, the functional nucleic acid forms an H-type pseudoknot in which the bases in a loop hybridize with a sequence from a distal single-stranded nucleic acid region. The pseudoknot structure of the functional nucleic acid is stable at temperatures normally used for hybridization of nucleic acids. In its pseudoknot configuration, the functional nucleic acid stem can unravel slightly to relieve the strain created in the functional nucleic acid loop by hybridization with the attenuator. This unraveling further distorts the functional nucleic acid and further decreases the probability that it will bind its target in the inactive state.

In another embodiment of the invention, the functional nucleic acid probe may comprise multiple functional nucleic acids. Each functional nucleic acid can specifically bind to the same or different target. For example, one functional nucleic acid may be an aptamer which specifically binds to a fluorescently labeled target in the presence of RAS oncogene mRNA. Another functional nucleic acid may be a ribozyme which inactivates the RAS oncogene mRNA. These exemplary multi-functional nucleic acid probes can carry out two independent functions in the presence of a single target. In another embodiment of the invention, the functional nucleic acid probe comprises multiple regulating nucleic acids each linked to a functional nucleic acid. Alternatively, the functional nucleic acid probes comprise multiple functional nucleic acids, regulating nucleic acids, and attenuators. Multi-functional probes can be applied simultaneously to diagnose, monitor, and treat a diseased cell in the presence of one or more corresponding signals.

"Amplification," as used herein, refers to the production of additional copies of a nucleic acid sequence and is generally carried out using PCR technologies well known in the art. The terms "antagonist" or "inhibitor," as used herein, refer to a molecule which, when bound to a target, blocks or modulates the biological or immunological activity of the target. Antagonists and inhibitors may include proteins, nucleic acids, carbohydrates, or any other molecules which bind to the target either covalently or non-covalently.

The term "antisense," as used herein, refers to nucleotide sequences which are complementary to a specific DNA or RNA sequence. The term "antisense strand" means a nucleic acid strand that is complementary to the "sense" strand. Antisense molecules may be produced by any method, including synthesis by ligating the gene(s) of interest in a reverse orientation to a viral promoter which permits the synthesis of a complementary strand. Once introduced into a cell, this transcribed strand combines with natural sequences produced by the cell to form duplexes. These duplexes then block further transcription or translation.

As used herein, "attenuator" refers to a molecule or compound capable of interfering with the activity of a functional nucleic acid when bound to the functional nucleic acid.

The terms "complementary" or "complementarity," as used herein, refer to the binding of polynucleotides under permissive salt and temperature conditions by base-pairing. For example, the sequence "A-G-T" binds to the complementary sequence "T-C-A". Complementarity between two single-stranded molecules may be "partial," in which only some of the nucleic acids bind, or it may be complete when total complementarity exists between the single stranded molecules. The degree of complementarity between nucleic acid strands has significant effects on the efficiency and strength of hybridization between nucleic acid strands. This is of particular importance in amplification reactions, which depend upon binding between nucleic acid strands.

As used herein, "functional nucleic acid" means a nucleic acid with the ability to bind to a specific target only when the nucleic acid is in a particular "activated" structural conformation.

"Nucleic acid sequence," as used herein, refers to an oligonucleotide, nucleotide, or polynucleotide, and fragments or portions thereof, and to DNA or RNA of genomic or synthetic origin which may be single- or double-stranded, and represent the sense or antisense strand.

As used herein, "regulating nucleic acid" refers to a nucleic acid capable of binding to a target and, when so bound, activating a functional nucleic acid.

The terms "specific binding" or "specifically binding," as used herein, in reference to the interaction of a nucleic acid with its target or ligand, mean that the interaction is dependent upon the presence of a particular structure (i.e., the binding site or region) on the nucleic acid; in other words, the nucleic acid recognizes and binds to a specific structure (e.g., nucleic acid, protein, and compound).

The probes of the present invention comprise functional nucleic acids capable of binding to a specific target. The functional nucleic acids are preferably single-stranded nucleic acids, which can fold into three-dimensional structures (conformations) forming binding regions, pockets, and other secondary or tertiary surfaces on the molecule. The binding site of the activated functional nucleic acid forms a highly specific complex with a particular target molecule. Functional nucleic acids include, but are not limited to, aptamers and ribozymes.

Figure 1:
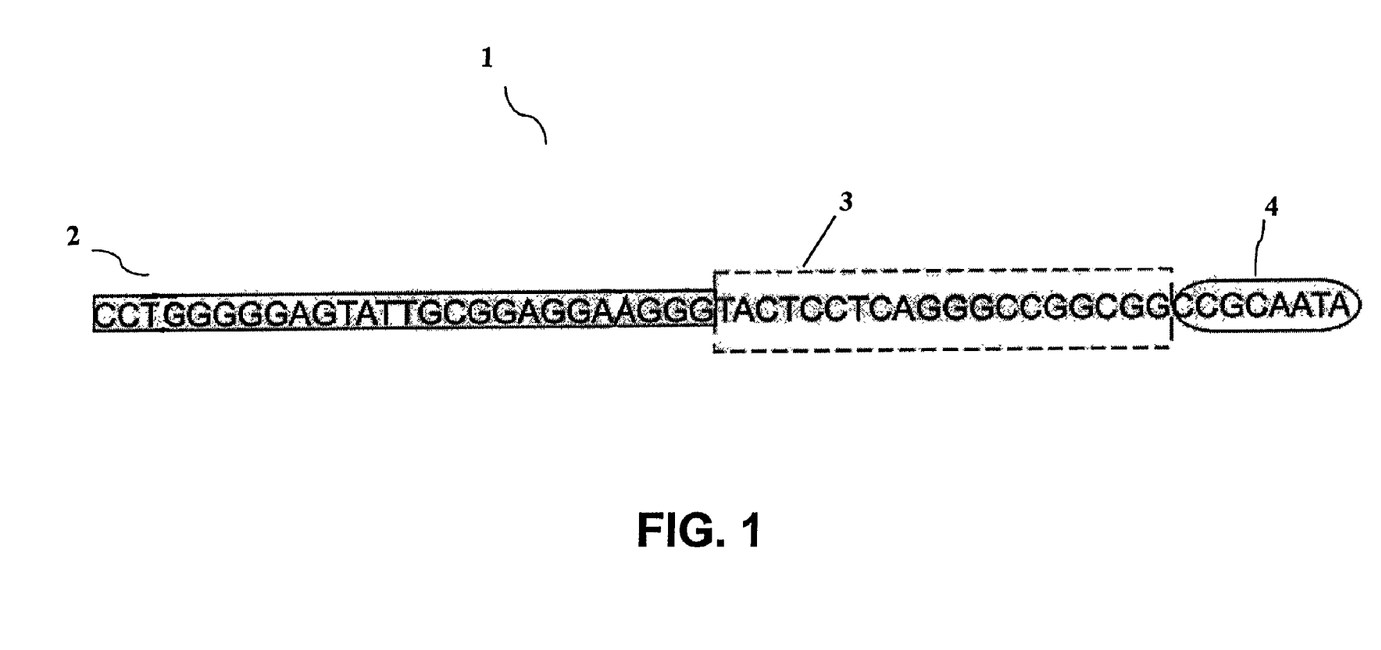
FIG. 1 depicts an exemplary functional nucleic acid probe (SEQ ID NO: 5) including a functional nucleic acid (SEQ ID NO: 1), a regulating nucleic acid (SEQ ID NO: 2), and an attenuator (SEQ ID NO: 3).

FIG. 1 illustrates a functional nucleic acid probe 1 in accordance with a preferred embodiment of the invention. With reference to FIG. 1, an exemplary functional nucleic acid probe 1 is shown. Functional nucleic acid probe 1 comprises a functional nucleic acid 2, a regulating nucleic acid 3, and an attenuator 4. The components comprising the exemplary functional nucleic acid probe 1 may be contiguous and cis-aligned, as shown in FIG. 1. The sequence of attenuator 4 is complementary to at least a portion of functional nucleic acid 2.

Figure 2A:
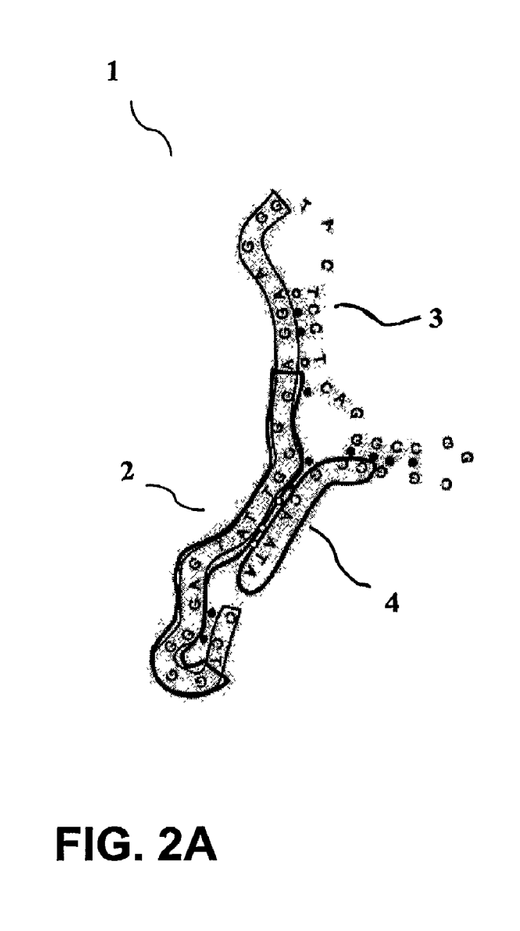
FIGS. 2a and 2b depict alternate structural conformations adopted by the functional nucleic acid probe (SEQ ID NO: 5) of FIG. 1 in the absence of the regulating nucleic acid target. The attenuator (oval) (SEQ ID NO: 3) is shown bound to the DNA-ATP aptamer (rectangle) (SEQ ID NO: 1).
Figure 2B:
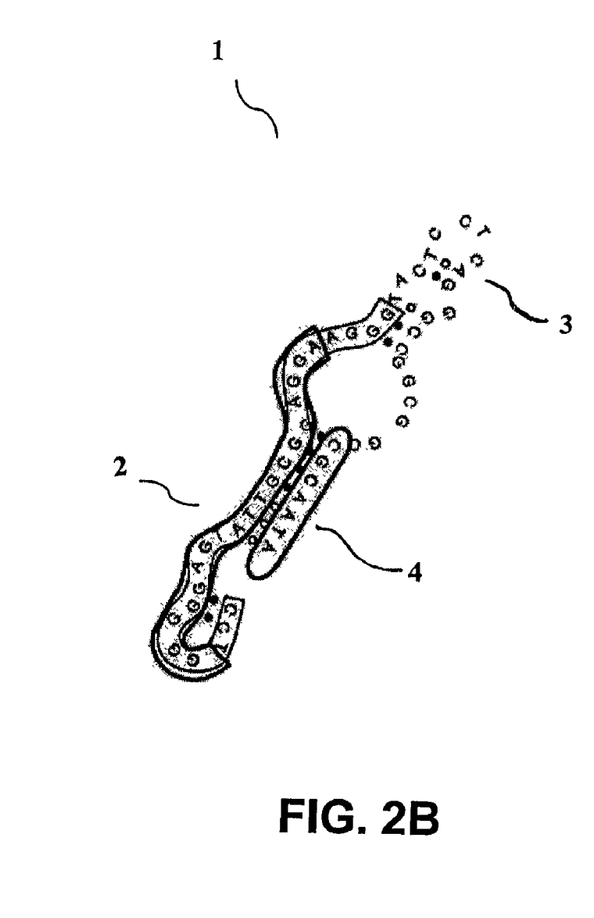

FIGS. 2a and 2b illustrate alternative inactive structural conformations adopted by functional nucleic acid probe 1 in the absence of a regulating nucleic acid target. The alternative inactive conformations were determined using Mfold, a software application used to predict the three-dimensional conformation of nucleic acid molecules. See A. E. Walter, D. H. Turner, J. Kim, M. H. Lyttle, P. Muller, D. H. Mathews and M. Zuker, *Coaxial stacking of helixes enhances binding of oligoribonucleotides and improves predictions of RNA folding,* Proc. Natl. Acad. Sci. USA 91, 9218–9222 (1994).

FIG. 2a depicts a presently preferred conformation in which attenuator 4 is hybridized solely to functional nucleic acid 2. Regulating nucleic acid 3 forms a loop structure in between functional nucleic acid 2 and attenuator 4. The filled circles show C-G hydrogen bonds and the open circles show A-T or non-Watson/Crick hydrogen bonds.

Figure 3:
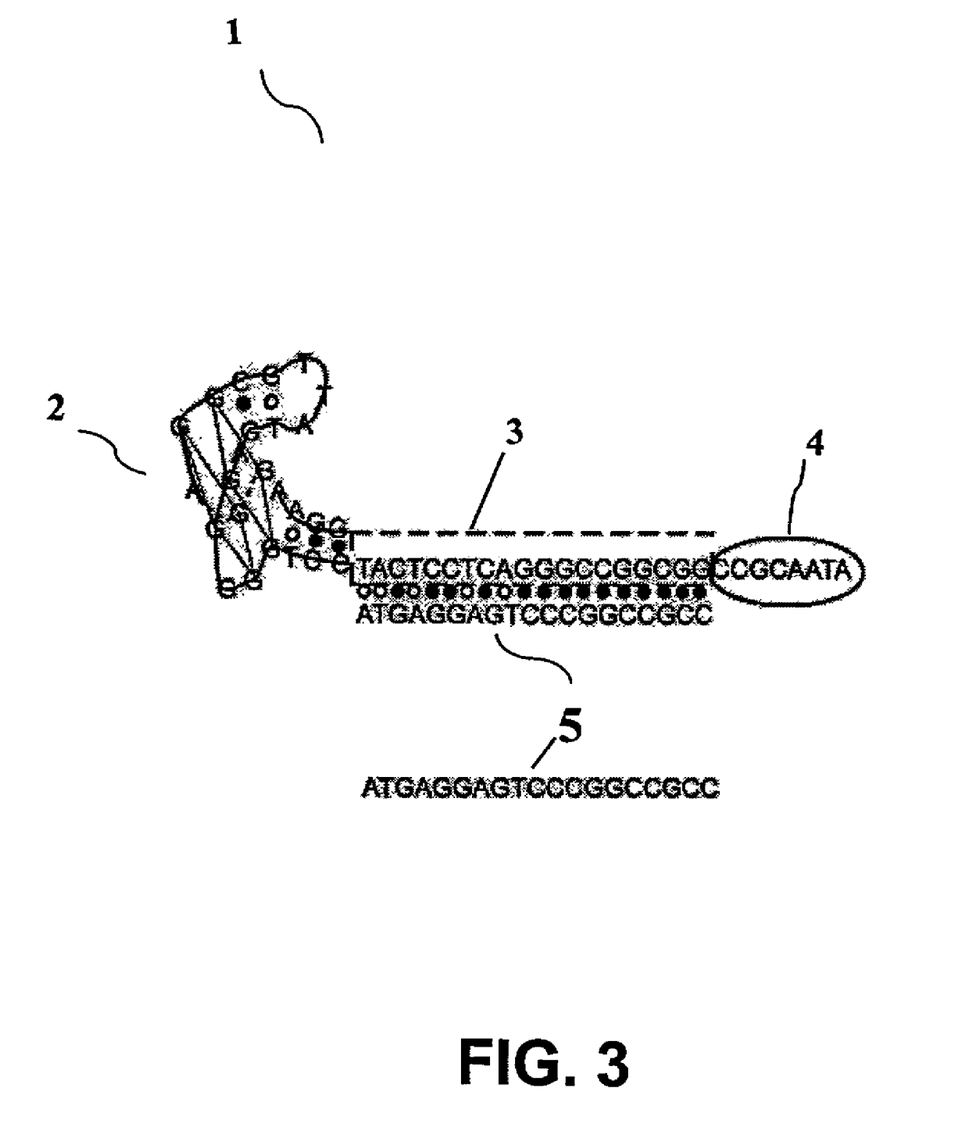
FIG. 3 depicts the structure adopted by the functional nucleic acid probe (SEQ ID NO: 5) of FIG. 1 in the presence of the regulating nucleic acid target (SEQ ID NO: 4). The functional nucleic acid (SEQ ID NO: 1) is shown in its active conformation. The regulating nucleic acid (SEQ ID NO: 2) is shown bound the regulating nucleic acid target (SEQ ID NO: 4).

FIG. 3 depicts the activated structure of functional nucleic acid probe 1. Nucleic acid target 5 binds to antisense sequence 3. Attenuator 4 is separated from DNA-ATP aptamer 2 by the Waston-Crick double-stranded complex of the antisense sequence 3 and nucleic acid target 5. DNA-ATP aptamer 2 is folded in its active confirmation following the binding of nucleic acid target 5 to antisense sequence 3.

In one embodiment, the functional nucleic acid probe binds its target after hybridization of the regulating nucleic acid target mRNA with the regulating nucleic acid. In another embodiment, a signaling mechanism (e.g., a fluorescent label or radionuclide) is conjugated with the functional nucleic acid target. Because the signaling mechanism is linked to the target but does not participate in the activation of the functional nucleic acid or contribute to recognition of or binding of the functional nucleic acid to its target, many different signal mechanisms can be exploited (e.g., fluorescence, radioactivity, chemiluminescence, and color signals). Furthermore, the signal generated by the binding of the functional nucleic acid probe to its labeled target can be amplified by a variety of currently available strategies well known in the art (e.g., use of a secondary labeled antibody, a labeled aptamer, or a tyramide detection system).

Functional nucleic acid probes comprised of nucleic acid can be generated in situ from a vector, such as vectors used in gene therapy. Thus, functional nucleic acid probes can be expressed in a desired cell or tissue by using an appropriate vector to express the probe in a desired location. Such targeted functional nucleic acid probes can be used for signaling gene expression in a particular cell type or targeting a diseased cell for killing or inactivation. In addition, expression of the functional nucleic acid probe can be placed under the control of an inducible promoter thus providing additional regulation of the probe. For example, expression of a functional nucleic acid probe designed to inactivate the expression of an oncogene can be induced by a promoter sensitive to the expression of an oncogenic protein.

In one embodiment of the invention, the functional nucleic acid is an aptamer capable of binding to a target molecule. Aptamers are nucleic acids that bind ligands with high specificity and high affinity and can be used, for example, to inhibit or interfere with the activity of nucleic acid or protein. Preferably, the affinity of an aptamer for its target is in the nanomolar range. Suitable aptamers can be selected using various techniques known in the art, such as "systematic evolution of ligands by exponential enrichment" or "SELEX". Tuerk and Gold, *Science* 249, 505 (1990); Ellington and Szostak, *Nature* 346, 818 (1990). In one embodiment, the aptamer forms a stem-loop structure in which the bases in the loop form the binding region for interaction with a target.

Aptamers can be designed to bind a variety of targets (e.g., proteins, nucleic acids, and compounds). For example, aptamers capable of binding proteins associated with a variety of diseases have recently been isolated. Sun, *Curr Opin Mol Ther,* 2(1), 100–105 (Feb. 2, 2000). These protein binding aptamers are used as antagonists and inhibit physiological functions associated with the protein target. Id. Aptamers capable of binding compounds such as theophylline, FMN, AMP, arginine, citruline, tobramycin, neomycin B have also been isolated and characterized. Hermann and Patel, *Science,* 287, 820–825 (2000). Aptamers can also be modified to increase their resistance to nucleases that may be encountered in cells or the bloodstream. Sun, *Curr Opin Mol Ther,* 2(1), 100–105 (Feb. 2, 2000). For example, modifying 2' OH groups of the nucleotide bases of an aptamer to F or $NH_2$ increases the half-life of an aptamer in blood. Id. Alternatively, aptamers can be attached to higher weight delivery vehicles to increase their resistance to nucleases or antibodies. Aptamers can be delivered to cells by a variety of techniques including, but not limited to, expression vectors, liposomes, viral vectors, and cell fusion.

In another embodiment of the invention, the functional nucleic acid is a ribozyme or deoxyribozyme ("nucleic acid enzymes"). Nucleic acid enzymes are naturally-occurring or synthetic nucleic acid structures capable of catalyzing cleavage of nucleic acid in a site-specific manner. Like aptamers and protein enzymes, nucleic acid enzymes form three-dimensional structures, which specifically interact with their substrates. Synthetic nucleic acid enzymes can be isolated through in vitro selection, in vivo selection, and in vitro evolution procedures. Rossi and Couture, *Intracellular Ribozyme Applications: Principles and Protocols,* (Horizon Press, July 1999).

The probes of the present invention comprise regulating nucleic acids for regulating the activity of a functional nucleic acid. Regulating nucleic acids serve as molecular switches for turning on or activating functional nucleic acids in the presence of specific targets. For example, with reference to the above-mentioned oncogene experiment, when an expressed oncogenic mRNA is present in the cell and binds to and forms a duplex with a regulating nucleic acid, the binding energy of the regulating nucleic acid/mRNA duplex forces the attenuator to be removed from the functional nucleic acid. In the absence of a bound attenuator, the functional nucleic forms its active, three-dimensional conformation and, for example, inactivate an oncogenic protein. Alternatively, the functional nucleic acid can be activated to bind to a labeled target molecule and entrap the label associated with the target thus identifying the presence of a cell expressing the oncogene. In another embodiment, the functional nucleic acid can be activated to kill the cell expressing the oncogene. Regulating nucleic acids provide a highly sensitive and specific signal in the presence of other targets. The functional nucleic acid probes of the invention may comprise one or more regulating nucleic acids.

The regulating nucleic acid is preferably of sufficient length to induce the removal of the attenuator from the functional nucleic acid and permit the functional nucleic acid to achieve its active conformation. In one embodiment, the regulating nucleic acid is greater in length than the attenuator. Preferably, the regulating nucleic acid is at least about 5 to about 200 base pairs, more preferably from about 10 to about 100 base pairs, and most preferably from about 8 to about 30 base pairs in length. The regulating nucleic acid is preferably designed to bind specifically to a regulating nucleic acid target.

In one embodiment, the regulating nucleic acid is an antisense nucleic acid. Antisense nucleic acids bind specifically to target complementary nucleic acid molecules. Alternatively, the regulating nucleic acid is an aptamer capable of specifically binding a target. Preferably, the functional nucleic acid is contiguous with the regulating nucleic acid. In another embodiment, the regulating nucleic acid is not contiguous with the functional nucleic acid and may be located, for example, on an expression vector that expresses a nucleic acid or protein, which directly interacts with the functional nucleic acid.

In a preferred embodiment of the invention the attenuator is an oligonucleotide nucleic acid sequence from about 3 to about 15 base pairs, more preferably from about 5 to 10 base pairs, and most preferably from about 6 to about 8 base pairs in length. In one embodiment, the attenuator binds to the functional nucleic acid and forms a duplex with fewer Watson-Crick base pairs than the duplex formed between the regulating nucleic acid and regulating nucleic acid target. The energy of the regulating nucleic acid/regulating nucleic acid target duplex overwhelms the energy of the attenuator/functional nucleic acid duplex, forcing removal of the attenuator from the functional nucleic acid. The attenuator-free functional nucleic acid can then assume its active, three-dimensional conformation.

In the absence of the regulating nucleic acid target, the attenuator preferably remains bound to the functional nucleic acid. In one embodiment, the attenuator is an aptamer or other nucleic acid sequence that binds or is complementary to at least a portion of the functional nucleic acid. Alternatively, the attenuator is a protein or compound capable of specifically binding to the functional nucleic acid.

In one embodiment of the invention, the attenuator is bound only to the functional nucleic acid and does not bind to or overlap with any portion of the regulating nucleic acid. If the attenuator were instead to overlap with both the functional nucleic acid and the regulating nucleic acid, it must be removed from (1) the regulating nucleic acid by strand displacement and (2) from the functional nucleic acid by the induced structural change in the probe. Such an overlapping attenuator must be designed to bind to both the functional nucleic acid and the regulating nucleic acid, thus limiting the available combinations of compatible functional nucleic acids and regulating nucleic acids. For example, an attenuator that is ⅓ complementary to the regulating nucleic acid and ⅔ complementary to the functional nucleic acid would require both strand displacement of ⅓ of the attenuator from the regulating nucleic acid and the formation of a regulating nucleic acid/target duplex to induce the remaining ⅔ of the attenuator from the functional nucleic acid. Furthermore, the overlapping region would have to be located in a "hot spot" subject to binding the regulating nucleic acid target when the regulating target is folded further limiting the compatible regulating nucleic acids available for use with a functional nucleic acid/attenuator combination. The modular nature of the preferred functional nucleic acid probes permits any functional nucleic acid to be used with virtually any regulating nucleic acid. Thus, removal of the attenuator is induced solely by the formation of a duplex between the regulating nucleic acid and the regulating nucleic acid target.

It is to be understood that the application of the teachings of the present invention to a specific problem or environment will be within the capabilities of one having ordinary skill in the art in light of the teachings contained herein. An exemplary product of the present invention and processes for its use appear in the following Example.

EXAMPLE 1

The following example illustrates the construction and method of using an exemplary functional nucleic acid probe made in accordance with the invention. A functional nucleic acid probe comprising a DNA-ATP aptamer (CCTGGGG-GAGTATTGCGGAGGAAGGG)(SEQ ID NO: 1), an antisense nucleic acid (TACTCCTCAGGGCCGGCGG)(SEQ ID NO: 2), and an attenuator (CCGCAATA)(SEQ ID NO: 3) is provided (FIG. 1). The DNA-ATP aptamer has a high affinity for the nucleotide adenosine when it is in its active conformation. The antisense nucleic acid is complementary to a segment of the RAS oncogene mRNA (ATGAG-GAGTCCCGGCCGCC)(SEQ ID NO: 4). The attenuator is an eight base pair oligonucleotide complementary to a region of DNA-ATP aptamer. In the absence of the RAS oncogene mRNA, the attenuator is bound to the DNA-ATP aptamer and maintains the DNA-ATP aptamer in its inactive conformation (FIG. 2). In the presence of the RAS oncogene mRNA, the antisense nucleic acid forms a duplex with the RAS oncogene mRNA (FIG. 3). The binding energy of the antisense nucleic acid/mRNA duplex overwhelms the binding energy of the DNA-ATP aptamer/attenuator duplex, forcing the attenuator off of the DNA-ATP aptamer. The DNA-ATP aptamer is now able to achieve its active conformation and bind to adenosine.

Figure 4:
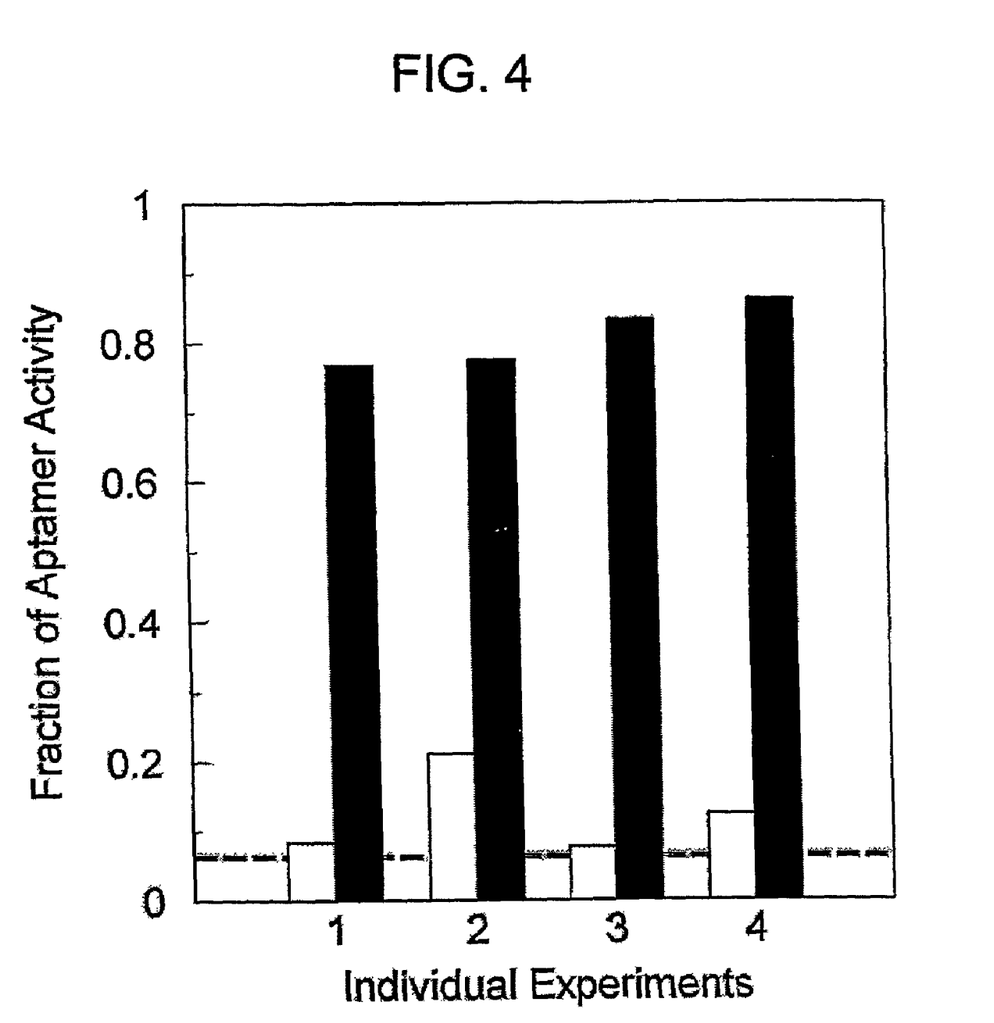
FIG. 4 demonstrates that the functional nucleic acid probe of FIG. 1 is activated only in the presence of the regulating nucleic acid target.

FIG. 4 demonstrates that the probe containing a DNA-ATP aptamer regulated by an attenuator is activated only in the presence of the RAS oncogene DNA oligonucleotide. With reference to FIG. 4, functional nucleic acid probe 1 was passed through an adenosine-sepharose column in the presence (solid bars) or absence (open bars) of the RAS oncogene DNA oligonucleotide in four separate experiments. The functional nucleic acid probe was radiolabeled with $P^{32}$ by end labeling with polynucleotide kinase. The samples were normalized to the total amount of P32 labeled DNA loaded on to the column. The amount of the functional nucleic acid probe bound to the column in the presence or absence of the RAS oncogene DNA oligonucleotide is expressed as a fraction of the binding activity achieved when a DNA-ATP aptamer was loaded on the same column. The functional nucleic acid probe was 80% as active as the DNA-ATP aptamer when the probe was loaded on the column after hybridization with the RAS oncogene DNA oligonucleotide. In contrast, the aptamer in the probe remained virtually inactive in the absence of the nucleic acid target. The specificity of the interaction between the aptamer and the adenosine-sepharose column was demonstrated by passing the functional nucleic acid probe through a column having adenosine with a free N6 position. The DNA-ATP aptamer is specific for N8 compared with N6 linked adenosine. The dashed line indicates that the DNA-ATP aptamer remained inactive when passed through an N6 linked adenosine column.

Figure 5:
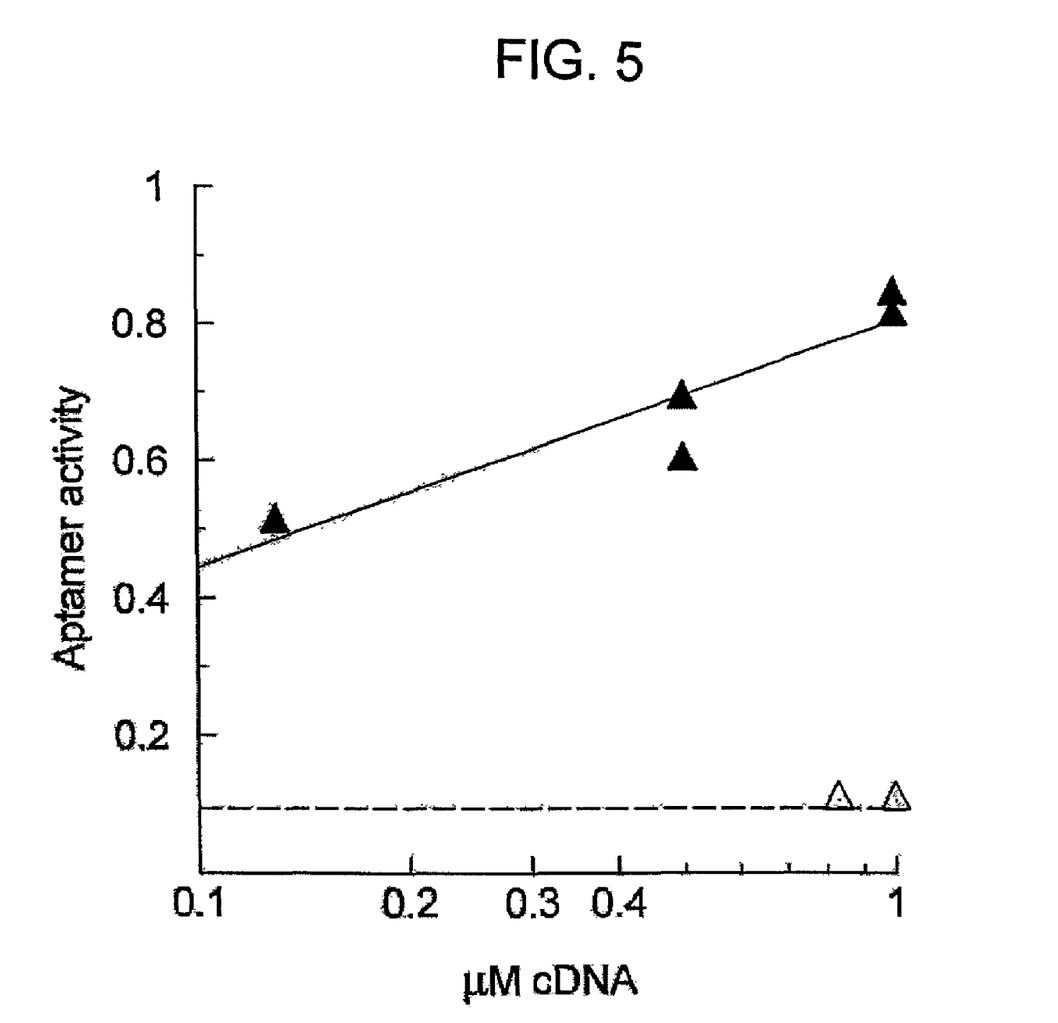
FIG. 5 shows a linear relationship between the activity of the functional nucleic acid probe of FIG. 1 and the amount of regulating nucleic acid target.

FIG. 5 shows a linear relationship between the amount of RAS oncogene DNA oligonucleotide added and the activity of the DNA-ATP aptamer in the functional nucleic acid probe. As the amount of RAS oncogene DNA oligonucleotide is increased from 0.1 uM to 1 uM, the activity of the DNA-ATP aptamer in the probe increases from approximately 0.4 to 0.8. The DNA-ATP aptamer of the functional nucleic acid probe is expressed relative to the activity of a DNA-ATP aptamer loaded on the column. The dashed line shows that a negligible amount of the DNA-ATP aptamer remained bound to the column in the absence of the RAS oncogene DNA oligonucleotide.

The above description is only illustrative of preferred embodiments which achieve the objects, features, and advantages of the present invention, and it is not intended that the present invention be limited thereto. Any modifications of the present invention which come within the spirit and scope of the following claims is considered part of the present invention. For example, functional nucleic acid probes can be used to detect nucleic acid sequences that are deposited on solid surfaces (e.g., Northern, Southern, and Matrix Arrays) or used in capture assays such as the ELISA method.

What is claimed as new and desired to be protected by Letters Patent of the United States is:

1. A method of activating a functional nucleic acid to bind to a functional nucleic acid target comprising:
   providing at least one functional nucleic acid, at least one regulating nucleic acid, and at least one attenuator wherein said functional nucleic acid is maintained in an inactive state by said attenuator, said attenuator does not bind to said regulating nucleic acid, and said regulating nucleic acid forms a loop structure between said functional nucleic acid and said attenuator;
   wherein said regulating nucleic acid binds to a regulating nucleic acid target, wherein binding of said regulating nucleic acid to said regulating nucleic acid target induces removal of said attenuator from said functional nucleic acid and activates said functional nucleic acid; and
   wherein said activated functional nucleic acid binds to said functional nucleic acid target.

2. The method of claim 1, wherein said functional nucleic acid is DNA.

3. The method of claim 1, wherein said functional nucleic acid is RNA.

4. The method of claim 1, wherein said functional nucleic acid is an aptamer.

5. The method of claim 1, wherein said functional nucleic acid is a ribozyme.

6. The method of claim 1, wherein said regulating nucleic acid is an antisense nucleic acid.

7. The method of claim 1, wherein said regulating nucleic acid target is a nucleic acid.

8. The method of claim 1, wherein said regulating nucleic acid is an aptamer.

9. The method of claim 1, wherein said regulating nucleic acid target is selected from the group consisting of nucleic acid, protein, and a chemical compound.

10. The method of claim 1, wherein said functional nucleic acid, said regulating nucleic acid, and said attenuator are arranged in cis.

11. The method of claim 1, wherein said functional nucleic acid, said regulating nucleic acid, and said attenuator are contiguous.

12. The method of claim 1, wherein the length of said regulating nucleic acid is greater than the length of said attenuator.

13. The method of claim 1, wherein said regulating nucleic acid is from about 5 to about 100 base pairs.

14. The method of claim 12, wherein said regulating nucleic acid is from about 8 to about 30 base pairs.

15. The method of claim 1, wherein said attenuator is from about 3 to about 15 base pairs.

16. The method of claim 14, wherein said attenuator is from about 6 to about 8 base pairs.

17. The method of claim 1, wherein binding energy generated by binding of said regulating nucleic acid to said regulating nucleic acid target is greater than binding energy generated by the binding of said attenuator to said functional nucleic acid.

* * * * *